United States Patent
Keller et al.

(10) Patent No.: US 11,976,030 B2
(45) Date of Patent: May 7, 2024

(54) PROCESS TO RECOVER HIGH QUALITY 3-METHYL-BUT-3-EN-1-OL

(71) Applicant: BASF SE, Ludwigshafen am Rhein (DE)

(72) Inventors: Andreas Keller, Ludwigshafen am Rhein (DE); Roland Minges, Minden (DE); Martin Kamasz, Ludwigshafen am Rhein (DE); Gabriele Gralla, Ludwigshafen am Rhein (DE); Bernhard Brunner, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 526 days.

(21) Appl. No.: 17/277,571

(22) PCT Filed: Sep. 13, 2019

(86) PCT No.: PCT/EP2019/074486
§ 371 (c)(1),
(2) Date: Mar. 18, 2021

(87) PCT Pub. No.: WO2020/058119
PCT Pub. Date: Mar. 26, 2020

(65) Prior Publication Data
US 2021/0355054 A1    Nov. 18, 2021

(30) Foreign Application Priority Data

Sep. 18, 2018  (EP) .................................... 18194973

(51) Int. Cl.
| | | |
|---|---|---|
| C07C 29/128 | (2006.01) | |
| B01J 31/02 | (2006.01) | |
| C07C 29/80 | (2006.01) | |
| C07C 29/84 | (2006.01) | |

(52) U.S. Cl.
CPC .......... C07C 29/84 (2013.01); B01J 31/0237 (2013.01); C07C 29/1285 (2013.01); C07C 29/80 (2013.01); B01J 2231/40 (2013.01); B01J 2531/002 (2013.01)

(58) Field of Classification Search
CPC ..................................................... C07C 29/095
See application file for complete search history.

(56) References Cited

U.S. PATENT DOCUMENTS

| | | | |
|---|---|---|---|
| 2,335,027 A | 11/1943 | Ritter | |
| 4,039,594 A * | 8/1977 | Stapp | ...................... C07C 33/05 |
| | | | 568/879 |
| 6,316,664 B1 | 11/2001 | Kratz et al. | |
| 9,868,681 B2 | 1/2018 | Suzuki | |

FOREIGN PATENT DOCUMENTS

| | | |
|---|---|---|
| CN | 103224444 A | 7/2013 |
| EP | 3305747 A1 | 4/2018 |
| GB | 1205397 A | 9/1970 |
| JP | 57-206628 A | 12/1982 |
| JP | 2000-500119 A | 1/2000 |
| WO | 02/51776 A2 | 7/2002 |
| WO | 2015/186699 A1 | 4/2017 |

OTHER PUBLICATIONS

European Search Report for EP Patent Application No. 18194973.6, dated Mar. 18, 2019, 3 pages.
International Preliminary Report on Patentability received for PCT Patent Application No. PCT/EP2019/074486, dated Apr. 1, 2021, 7 pages.
International Search Report and Written Opinion received for PCT Patent Application No. PCT/EP2019/074486, dated Oct. 17, 2019, 8 pages.

* cited by examiner

*Primary Examiner* — Medhanit W Bahta
(74) *Attorney, Agent, or Firm* — Faegre Drinker Biddle & Reath LLP

(57) ABSTRACT

The presently claimed invention relates to a process for the recovery of 3-methyl-3-buten-1-ol from a stream obtained in the production of 3-methyl-3-buten-1-ol from 2-methyl-prop-1-ene and formaldehyde, by treating the stream with an amine catalyst.

16 Claims, No Drawings

PROCESS TO RECOVER HIGH QUALITY 3-METHYL-BUT-3-EN-1-OL

CROSS-REFERENCE TO RELATED APPLICATIONS

This application is a national stage application (under 35 U.S.C. § 371) of PCT/EP2019/074486, filed Sep. 13, 2019, which claims benefit of European Application No. 18194973.6, filed Sep. 18, 2019, both of which are incorporated herein by reference in their entirety.

FIELD OF THE INVENTION

The presently claimed invention relates to a process for the recovery of 3-methyl-3-buten-1-ol from a stream obtained in the production of 3-methyl-3-buten-1-ol, from 2-methylprop-1-ene and formaldehyde, by treating the stream with an amine catalyst.

BACKGROUND OF THE INVENTION

3-Methyl-3-buten-1-ol as such is useful as the initiator for the synthesis of polycarboxylic acid concrete superplasticizer. In addition, 3-methyl-3-buten-1-ol can be isomerized to iso-pentenyl alcohol, which is used as a main raw material for synthesizing a probiotic pesticide, methyl ethyl benzoate. The 3-methyl-3-buten-1-ol is also a starting material for the manufacture of dyes, pharmaceuticals, plastics and scents and specially to produce citral.

The synthesis of 3-methyl-3-buten-1-ol from reaction of 2-methylprop-1-ene and formaldehyde is known from the literature.

The GB 1,205,397 describes the reaction of 2-methylprop-1-ene with formaldehyde in the presence of tin chloride. A disadvantage of this method is that 3-methyl-3-buten-1-ol is obtained only with a selectivity of not more than 22%.

The WO 02/051776 describes a method of preparing an γ,δ-unsaturated alcohol by reacting an α-olefin with an aldehyde in the presence of a phosphate as the basic compound.

The U.S. Pat. No. 2,335,027 discloses a method for the thermal synthesis of 3-methyl-3-buten-1-ol from formaldehyde and isobutylene.

The widely known disadvantage associated with this reaction is that the by-production amount of formic acid reacts with the 3-methyl-3-buten-1-ol during the reaction to form undesired 3-methyl-but-3-en-1-yl formate. Also, the contamination of 3-methyl-3-buten-1-ol with 3-methyl-but-3-en-1-yl formate deteriorates the purity, yield and quality of 3-methyl-3-buten-1-ol.

As a method of solving the aforementioned problem, U.S. Pat. No. 9,868,681 describes a process for the preparation of 3-methyl-3-buten-1-ol, whereby a reaction liquid is obtained by reacting 2-methylprop-1-ene with formaldehyde in the presence of tert.-butanol. The reaction liquid is stirred with an aqueous alkaline solution to obtain an aqueous solution of pH 12.8. As a result, the by-products formic acid and formic acid ester are converted into formate and are removed. Also, 3-methyl-3-buten-1-ol is formed from the ester moiety of formic acid ester.

However, the synthesis has some drawbacks.

Within the high-pressure reaction of 2-methylprop-1-ene with formaldehyde, 1% to 3% of the aldehyde 3-methyl-but-2-enal are formed, which is also a value product for the citral process. However, 3-methyl-but-2-enal is decomposed under basic reaction conditions and, subsequently, the decomposition results in lower overall yields for 3-methyl-3-buten-1-ol and 3-methyl-but-2-enal.

3-Methyl-2-buten-1-ol is soluble to a certain degree in aqueous solutions (90 g/l at 20° C. in pure water) and therefore also soluble in the aqueous NaOH phase. For the reduction of 3-methyl-2-buten-1-ol losses in the inorganic NaOH-phase, further process steps for re-extraction or distillation of 3-methyl-2-buten-1-ol are necessary.

U.S. Pat. No. 9,868,681 also points out that the temperatures during the contact of the reaction liquid with the alkaline aqueous solution should be 10° C. to 90° C. However, in the case of industrial application, this would require an extensive and tedious step of cooling the reaction liquid from a temperature of 330° to a temperature of 90° C. Another challenge of the process described in U.S. Pat. No. 9,868,681 is the removal of Na-bearing impurities and effluents in the organic phase at industrial scale.

It is accordingly an object of the presently claimed invention to counter the disadvantages described in the prior art and meet the requirements arising from the prior art and provide a process for the production of 3-methyl-3-buten-1-ol which is easy to carry out industrially, does not generate any noteworthy amounts of salts as by-products and leads to high over-all yields of 3-methyl-butenol-ol.

SUMMARY OF THE INVENTION

Surprisingly, it was found that 3-methyl-but-3-en-1-ol can be recovered from a stream comprising 3-methyl-but-3-en-1-yl formate, water and methanol in the presence of an amine catalyst, so that the overall yield of the process to produce 3-methyl-but-3-en-1-ol is increased. The stream is generated in the synthesis of 3-methyl-but-3-en-1-ol from 2-methylprop-1-ene and formaldehyde.

Hence, the presently claimed invention is directed, in one aspect, to a process for the recovery of 3-methyl-but-3-en-1-ol from a stream comprising 3-methyl-but-3-en-1-yl formate, ≥0.01 wt. % to 10 wt. % water and 50 wt. % to 70 wt. % methanol, each based on the total weight of the stream, comprising at least the steps of:

A) contacting at least one amine catalyst with the stream to obtain a treated stream;
B) subjecting the treated stream to a temperature in the range of ≥40° C. to ≤120° C. to obtain 3-methyl-but-3-en-1-ol; and
C) removing 3-methyl-but-3-en-1-ol from the treated stream.

In another aspect, the presently claimed invention is also directed to a process for providing the stream comprising 3-methyl-but-3-en-1-yl formate, ≥0.01 wt. % to ≤10 wt. % water and ≥50 wt. % to ≤70 wt. % methanol each based on the total weight of the stream, wherein the process comprises at least the steps of:

a) reacting 2-methylprop-1-ene and formaldehyde to obtain a mixture comprising 3-methyl-but-3-en-1-ol, methanol, water and 3-methyl-but-3-en-1-yl formate;
b) separating the mixture obtained in step a) into an organic phase comprising at least 3-methyl-but-3-en-1-ol, methanol and 3-methyl-but-3-en-1-yl formate and an aqueous phase comprising water and ≤10 wt. % 3-methyl-but-3-en-1-ol;
c) subjecting the organic phase obtained in step b) to a temperature in the range of ≥120° C. to 160° C. to separate a light boiling fraction comprising water, methanol, 3-methyl-but-3-en-1-yl formate from 3-methyl-but-3-en-1-ol;

d) combining the aqueous phase from step b) and the light boiling fraction of step c) and subjecting the combined phases to a temperature in the range of ≥85° C. to ≤105° C. to remove at least 70% water of the total amount of water to obtain a drained stream; and e) subjecting the drained stream of step d) to a temperature in the range of ≥85° C. to ≤100° C., to obtain the stream comprising 3-methyl-but-3-en-1-yl formate, ≥0.01 wt. % to ≤10 wt. % water and ≥50 wt. % to ≤70 wt. % methanol, each based on the total weight of the stream.

In yet another aspect, the presently claimed invention is also directed to a process for the production of 3-methyl-but-3-en-1-ol comprising at least the step of aa) reacting 2-methylprop-1-ene and formaldehyde to obtain a mixture comprising 3-methyl-but-3-en-1-ol, methanol, water and 3-methyl-but-3-en-1-yl formate;

bb) separating the mixture obtained in step aa) into an organic phase comprising at least 3-methyl-but-3-en-1-ol, methanol and 3-methyl-but-3-en-1-yl formate and an aqueous phase comprising water and ≤10 wt. % 3-methyl-but-3-en-1-ol;

cc) subjecting the organic phase obtained in step bb) to a temperature in the range of ≥120° C. to ≤160° C. to separate a light boiling fraction comprising water, methanol, 3-methyl-but-3-en-1-yl formate from 3-methyl-but-3-en-1-ol; and dd) combining 3-methyl-but-3-en-1-ol obtained in step cc) with 3-methyl-but-3-en-1-ol obtained by the recovery process according to the presently claimed invention to obtain combined 3-methyl-but-3-en-1-ol.

DETAILED DESCRIPTION OF THE INVENTION

In the present specification, the restrictive wording with "being preferred" can be arbitrarily selected, and a combination of restrictive wordings with "being preferred" may be said to be more preferred.

Starting materials used in the process are commercially available or can be prepared by methods known in the literature.

The "presently claimed invention", "invention" or "process of the presently claimed invention" refers to one or more of the steps A), B) and C) or steps a), b), c), d), e) or steps aa), bb), cc) and dd).

Although the presently claimed invention will be described with respect to particular embodiments, this description is not to be construed in a limiting sense.

Before describing in detail exemplary embodiments of the presently claimed invention, definitions important for understanding the presently claimed invention are given. As used in this specification and in the appended claims, the singular forms of "a" and "an" also include the respective plurals unless the context clearly dictates otherwise. In the context of the presently claimed invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%. It is to be understood that the term "comprising" is not limiting. For the purposes of the presently claimed invention the term "consisting of" is considered to be a preferred embodiment of the term "comprising of". If hereinafter a group is defined to comprise at least a certain number of embodiments, this is meant to also encompass a group which preferably consists of these embodiments only.

In case the terms "first", "second", "third" or "A)", "B)", "C)", AA), BB), CC), "(a)", "(b)", "(c)", "(d)", "i", "ii" etc. relate to steps of a method or use or assay there is no time or time interval coherence between the steps, i.e. the steps may be carried out simultaneously or there may be time intervals of seconds, minutes, hours, days, weeks, months or even years between such steps, unless otherwise indicated in the application as set forth herein above or below. It is to be understood that this invention is not limited to the particular methodology, protocols, reagents etc. described herein as these may vary. It is also to be understood that the terminology used herein is for the purpose of describing particular embodiments only and is not intended to limit the scope of the presently claimed invention that will be limited only by the appended claims. Unless defined otherwise, all technical and scientific terms used herein have the same meanings as commonly understood by one of ordinary skill in the art.

The presently claimed invention is directed to a process for the recovery of 3-methyl-but-3-en-1-ol from a stream comprising 3-methyl-but-3-en-1-yl formate, ≥0.01 wt. % to ≤10 wt. % water and ≥50 wt. % to ≤70 wt. % methanol each based on the total weight of the stream, comprising at least the steps of:

A) contacting at least one amine catalyst with the stream to obtain a treated stream;

B) subjecting the treated stream to a temperature in the range of 40° C. to 120° C. to obtain 3-methyl-but-3-en-1-ol; and p0 C) removing 3-methyl-but-3-en-1-ol from the treated stream.

In one embodiment, the presently claimed invention is directed to a process for providing the stream comprising 3-methyl-but-3-en-1-yl formate, ≥0.01 wt. % to ≤10 wt. % water and ≥50 wt. % to ≤70 wt. % methanol each based on the total weight of the stream, wherein the process comprises at least the steps of:

a) reacting 2-methylprop-1-ene and formaldehyde to obtain a mixture comprising 3-methyl-but-3-en-1-ol, methanol, water and 3-methyl-but-3-en-1-yl formate;

b) separating the mixture obtained in step a) into an organic phase comprising at least 3-methyl-but-3-en-1-ol, methanol and 3-methyl-but-3-en-1-yl formate and an aqueous phase comprising at least water and ≤10 wt. % 3-methyl-but-3-en-1-ol;

c) subjecting the organic phase obtained in step b) to a temperature in the range of ≥120° C. to ≤160° C. to separate a light boiling fraction comprising water, methanol, 3-methyl-but-3-en-1-yl formate from 3-methyl-but-3-en-1-ol d) combining the aqueous phase from step b) and the light boiling fraction of step c) and subjecting the combined phases to a temperature in the range of ≥85° C. to ≤105° C. to remove at least 70% water of the total amount of water to obtain a drained stream; and e) subjecting the drained stream of step d) to a temperature in the range of ≥85° C. to ≤100° C., to obtain the stream comprising 3-methyl-but-3-en-1-yl formate, ≥0.01 wt. % to ≤10 wt. % water and ≥50 wt. % to ≤70 wt. % methanol, each based on the total weight of the stream.

The formaldehyde used in step a) can be used in gaseous form, in polymeric form or in the form of an aqueous solution. Though formaldehyde may be used as it is, one having been dissolved in a solvent can also be used. Though the solvent that dissolves formaldehyde therein is not particularly limited, it is preferably water from the standpoint of easy availability, namely it is preferred to use a formaldehyde aqueous solution (formalin). In addition, from the viewpoint of volumetric efficiency, it is preferred that the concentration of formaldehyde is higher. However, when the concentration of formaldehyde is too high, a problem of deposition is caused, resulting in making its handling difficult. Thus, the concentration of the formaldehyde solution is preferably 10 to 70 wt. %, more preferably 30 to 60 wt. %, yet more preferably a solution containing 35 wt. % to 55 wt. % is used.

In yet another embodiment, aqueous formaldehyde is being preferred.

In one embodiment, preferably 1.0 to 60.0 mol, more preferably 2.0 to 30.0 mol, yet more preferably 3.0 to 30.0 mol, most preferably 2.0 to 15.0 mol, and in particular 3.0 to 15.0 mol of 2-methylprop-1-ene to 1.0 mol formaldehyde are used.

In another embodiment, the step a) can be carried out in the presence or absence of a solvent. Preferably, the step a) is carried out in the absence of any solvent.

In yet another embodiment, the step a) can be carried out in the presence or absence of an amine.

In yet another embodiment, the step a) is, preferably, carried out in the presence of an amine. In yet another embodiment, the amine is selected from the group consisting of trimethylamine, dimethylamine, triethylamine, diethylamine, triisopropylamine, diisopropylamine, 1-propylamine, butan-2-amine, methylpropan-2-amine, ethane-1,2-diamine, urotropine, pyridine and piperidine. In another embodiment, the amine is, preferably, selected from group consisting of urotropine, triethylamine and trimethylamine. Preferably, the amine is urotropine.

In yet another embodiment, the reaction temperature in step a) is preferably in the range of 180° C. to 350° C., more preferably in the range of 220° C. to 300° C., yet more preferably in the range of 240° C. to 280° C.

In yet another embodiment, the reaction pressure in step a) is preferably in the range of 30 bar to 300 bar, more preferably in the range of 50 bar to 280 bar, yet more preferably in the range of 100 bar to 280 bar, most preferably in the range of 150 bar to 250 bar.

In yet another embodiment, the reaction of step a) is preferably carried out in a batch mode, semi-batch mode or continuous mode. The step a) is more preferably carried out in the continuous mode.

Preferably, a mixed solution containing the 2-methylprop-1-ene and the aqueous formaldehyde solution in predetermined ratios is fed into a reaction vessel which is heated at a predetermined temperature. The reaction pressure is regulated and is kept at a predetermined pressure. The aforementioned mixed solution is allowed to stay within the reaction vessel for a predetermined time of about 0.025 hours to about 5.0 hours, preferably 0.05 hours to about 2.0 hours, more preferably for about 0.05 hours to about 1.5 hours to obtain reaction mixture. The reaction mixture is cooled.

In yet another embodiment, the mixture comprising 3-methyl-but-3-en-1-ol, methanol, water and 3-methyl-but-3-en-1-yl formate is obtained from step a). The condensates of the mixture obtained from step a) consists of two phases, namely the upper organic phase and the lower aqueous phase.

In yet another embodiment, the mixture obtained from step a) is separated in step b) into an organic phase comprising at least 3-methyl-but-3-en-1-ol, methanol and 3-methyl-but-3-en-1-yl formate and an aqueous phase comprising at least water and 10 wt. % 3-methyl-but-3-en-1-ol, based on the total weight of an aqueous phase.

In yet another embodiment, the organic phase obtained in step b) is subjected to a temperature in the range of ≥120° C. to ≤160° C. to separate a light boiling fraction comprising water, methanol, 3-methyl-but-3-en-1-yl formate from 3-methyl-but-3-en-1-ol. In yet another embodiment, the light boiling fraction comprising at least 3-methyl-but-3-en-1-ol, methanol and 3-methyl-but-3-en-1-yl formate obtained in step b) is subjected to a temperature in the range of ≥120° C. to ≤160° C. in a distillation column at the pressure is in the range of ≥50 to ≤300 mbar.

In another embodiment, the aqueous phase obtained in step b) comprises at least water and ≥10 wt. % 3-methyl-but-3-en-1-ol, based on the total weight of an aqueous phase. In yet another embodiment, the aqueous phase from step b) is combined with the light boiling fraction comprising water, methanol, 3-methyl-but-3-en-1-yl formate of step c).

In yet another embodiment, the combined phase is subjected to a temperature in the range of ≥85° C. to ≤105° C. to remove at least 70% water of the total amount of water to obtain the drained stream.

In yet another embodiment, the drained stream of step d) is subjected to the temperature in the range of ≥85° C. to ≤100° C., to obtain a stream comprising 3-methyl-but-3-en-1-yl formate, preferably ≥1 wt. % to ≤25 wt. % 3-methyl-but-3-en-1-yl formate, 0.01 wt. % to ≤10 wt. % water; preferably ≥3 wt. % to ≤8 wt. % water, and ≥50 wt. % to ≤70 wt. % methanol, preferably ≥55 wt. % to ≤70 wt. % methanol each based on the total weight of the stream.

In yet another embodiment, the stream comprising 3-methyl-but-3-en-1-yl formate, ≥0.01 wt. % to ≤10 wt. % water and ≥50 wt. % to ≤70 wt. % methanol each based on the total weight of the stream, further comprises residual amine i.e. the at least one amine is residual amine that is used for the synthesis of 3-methyl-but-3-en-1-ol from 2-methylprop-1-ene and formaldehyde.

In one embodiment, the presently claimed invention provides a process for recovery of 3-methyl-but-3-en-1-ol from a stream comprising 3-methyl-but-3-en-1-yl formate, ≥0.01 wt. % to ≤10 wt. % water and ≥50 wt. % to ≤70 wt. % methanol each based on the total weight of the stream, comprising at least the steps of:

A) contacting at least one amine catalyst with the stream to obtain a treated stream;
B) subjecting the treated stream to a temperature in the range of ≥40° C. to ≤120° C. to obtain 3-methyl-but-3-en-1-ol; and
C) removing 3-methyl-but-3-en-1-ol from the treated stream.

In another embodiment, the stream comprises 3-methyl-but-3-en-1-yl formate in an amount in the range of ≥1 wt. % to ≤25 wt. %, preferably ≥5 wt. % to ≤25 wt. %, based on the total weight of the stream.

In yet another embodiment, the stream comprises 3-methyl-but-3-en-1-ol in an amount in the range of ≥0.001 wt. % to ≤10 wt. %, based on the total weight of the stream. In yet another embodiment, the stream comprises the at least one residual amine that is used for the synthesis of 3-methyl-but-3-en-1-ol from 2-methylprop-1-ene and formaldehyde.

In yet another embodiment, the stream comprises 3-methyl-but-3-en-1-yl formate, preferably ≥1 wt. % to ≤25 wt. % 3-methyl-but-3-en-1-yl formate; ≥0.01 wt. % to ≤10 wt. % water, preferably ≥3 wt. % to ≤8 wt. % water; and ≥50 wt. % to ≤70 wt. % methanol, preferably ≥55 wt. % to ≤70 wt. % methanol each based on the total weight of the stream.

In yet another embodiment, the stream comprises ≥1 wt. % to ≤25 wt. % 3-methyl-but-3-en-1-yl formate, ≥0.01 wt. % to ≤10 wt. % water, ≥50 wt. % to ≤70 wt. % methanol, ≥0.001 wt. % to ≤1 wt. % formic acid, ≥0 wt. % to ≤10 wt. % 3-methyl-but-3-en-1-ol and <0.5 wt. % of 3-methyl-but- 2-enal, whereby the amount of wt. % are based on the total weight of the stream and add up to 100 wt. %.

In yet another embodiment, the stream comprises ≥5 wt. % to ≤25 wt. % 3-methyl-but-3-en-1-yl formate, ≥0.01 wt. % to ≤10 wt. % water, ≥50 wt. % to ≤70 wt. % methanol, ≥0.001 wt. % to ≤1 wt. % formic acid, ≥0.001 wt. % to ≤10 wt. % 3-methyl-but-3-en-1-ol and the at least one residual amine that is used for the synthesis of 3-methyl-but-3-en-1-ol from 2-methylprop-1-ene and formaldehyde, whereby the amount of wt. % are based on the total weight of the stream and add up to 100 wt. %.

In one embodiment, the at least one amine catalyst is contacted in step A) with the stream comprising 3-methyl-but-3-en-1-yl formate, ≥0.01 wt. % to ≤10 wt. % water and ≥50 wt. % to ≤70 wt. % methanol, each based on the total weight of the stream, to obtain a treated stream.

In another embodiment, the at least one amine catalyst is contacted in step A) to the stream comprising 3-methyl-but-3-en-1-yl formate, preferably ≥1 wt. % to ≤25 wt. % 3-methyl-but-3-en-1-yl formate; ≥0.01 wt. % to ≤10 wt. % water, preferably ≥3 wt. % to ≤8 wt. % water; and ≥50 wt. % to ≤70 wt. % methanol, preferably ≥55 wt. % to ≤70 wt. % methanol; each based on the total weight of the stream.

In another embodiment, the at least one amine catalyst is contacted in step A) to the stream comprising 3-methyl-but-3-en-1-yl formate, preferably ≥1 wt. % to ≤25 wt. % 3-methyl-but-3-en-1-yl formate; ≥0.01 wt. % to ≤10 wt. % water, preferably ≥3 wt. % to ≤8 wt. % water; and ≥50 wt. % to ≤70 wt. % methanol, preferably ≥55 wt. % to ≤70 wt. % methanol; and the at least one residual amine that is used for the synthesis of 3-methyl-but-3-en-1-ol from 2-methylprop-1-ene and formaldehyde, each based on the total weight of the stream.

In one embodiment, the at least one amine catalyst is contacted to the stream comprising 3-methyl-but-3-en-1-yl formate, ≥0.01 wt. % to ≤10 wt. % water and ≥50 wt. % to ≤70 wt. % methanol, each based on the total weight of the stream, in a distillation column. In another embodiment, no additional methanol is added to the stream comprising 3-methyl-but-3-en-1-yl formate, ≥0.01 wt. % to ≤10 wt. % water and ≥50 wt. % to ≤70 wt. % methanol, each based on the total weight of the stream, in a distillation column.

The at least one amine catalyst is added to the stream comprising 3-methyl-but-3-en-1-yl formate, ≥0.01 wt. % to ≤10 wt. % water and ≥50 wt. % to ≤70 wt. % methanol, each based on the total weight of the stream, such that the pH of the treated stream is in the range of pH 7.0 to 9.5; preferably in the range of pH 7.5 to 9.5; more preferably in the range of pH 7.5 to 9.0, yet more preferably in the range of pH 8.0 to 9.5; yet more preferably in the range of pH 8.0 to 9.0; most preferably in the range of pH 8.5 to 9.0, most preferably in the range of pH 8.5 to 9.0; in particular in the range of pH 8.5 to 9.5.

In yet another embodiment, the boiling point of the at least one amine catalyst is in the range of ≥2° C. to ≤130° C.

In another embodiment, the at least one amine catalyst of step A) is selected from the group consisting of trimethylamine, dimethylamine, triethylamine, diethylamine, triisopropylamine, diisopropylamine, 1-propylamine, butan-2-amine, methylpropan-2-amine, ethane-1,2-diamine, pyridine and piperidine. Preferably, the at least one amine is trimethylamine or triethylamine.

In another embodiment, the at least one amine catalyst is present in an amount in the range of ≥0.001 to ≤5.0 wt. %, based on the total weight of the stream, preferably ≥0.01 to ≤4.0 wt. %, more preferably ≥0.05 to ≤4.0 wt. %, even more preferably ≥0.1 to ≤4.0 wt. %, yet more preferably ≥0.5 to ≤4.0 wt. %, most preferably ≥1.0 to ≤4.0 wt. % based on the total weight of the stream.

In one embodiment, the treated stream of step A) is subjected to a temperature in the range of ≥40° C. to ≤120° C., preferably in the range of ≥60° C. to ≤110° C. In another embodiment, the treated stream of step A) is subjected to a temperature in the range of ≥40° C. to ≤120° C. in a distillation column to obtain at least the 3-methyl-but-3-en-1-ol. The 3-methyl-but-3-en-1-ol, so obtained, is removed through the side draw of a distillation column.

In another embodiment, the treated stream of step A) is subjected to a temperature in the range of ≥40° C. to ≤120° C. in a distillation column to further obtain at least methylformate, methanol and at least one amine. The at least methylformate, methanol and the at least one amine are removed with the distillate, i.e. the head stream of the distillation column.

In one embodiment, the process for recovery of 3-methyl-but-3-en-1-ol from a stream comprising 3-methyl-but-3-en-1-yl formate, ≥0.01 wt. % to ≤10 wt. % water and ≥50 wt. % to ≤70 wt. % methanol, each based on the total weight of the stream, is performed in a reactive distillation.

In one embodiment, the steps A) to C) of the process for recovery of 3-methyl-but-3-en-1-ol from a stream comprising 3-methyl-but-3-en-1-yl formate, ≥0.01 wt. % to ≤10 wt. % water and ≥50 wt. % to ≤70 wt. % methanol, each based on the total weight of the stream, is performed in a reactive distillation.

In yet another embodiment, the steps A) to C) are preferably carried out in a batch mode, semi-batch mode and continuous mode. The steps A) to C) are more preferably carried out in a continuous mode.

In yet another embodiment, the process for recovery of 3-methyl-but-3-en-1-ol from a stream comprising 3-methyl-but-3-en-1-yl formate, ≥0.01 wt. % to ≤10 wt. % water and ≥50 wt. % to ≤70 wt. % methanol, each based on the total weight of the stream, is a continuous process.

In yet another embodiment, the steps A) to C) are carried out simultaneously.

In another embodiment, the steps A), B) and C) are performed continuously in a reactive distillation by the removal of 3-methyl-but-3-en-1-ol through the side draw of a distillation column and removal of methylformate, methanol and at least one amine with the distillate, i.e. the head stream of the distillation column.

In another embodiment, the reaction of 3-methyl-but-3-en-1-yl formate with methanol in the presence of at least one amine catalyst is conducted at the temperature in the range of ≥40° C. to ≤120° C. in a reactive distillation. The at least one amine catalsyst acts as a transesterification catalyst. In the process, the 3-methyl-but-3-en-1-yl formate is converted into 3-methyl-but-3-en-1-ol and at the same time methanol is converted into methyl formate.

In another embodiment, the methyl formate is readily separated from the reaction mixture with the distillate, i.e. the head stream of the distillation column.

In one embodiment, the presently claimed invention also provides a process for the production of 3-methyl-but-3-en-1-ol comprising at least the steps of:

aa) reacting 2-methylprop-1-ene and formaldehyde to obtain a mixture comprising 3-methyl-but-3-en-1-ol, formic acid, methanol, water and 3-methyl-but-3-en-1-yl formate;

bb) separating the mixture obtained in step aa) into an organic phase comprising at least 3-methyl-but-3-en-1-ol, methanol and 3-methyl-but-3-en-1-yl formate and an aqueous phase comprising water and ≤10 wt. % 3-methyl-but-3-en-1-ol;

cc) subjecting the organic phase obtained in step bb) to a temperature in the range of ≥120° C. to ≤160° C. to separate a light boiling fraction comprising water, methanol and 3-methyl-but-3-en-1-yl formate from 3-methyl-but-3-en-1-ol; and dd) combining 3-methyl-but-3-en-1-ol obtained in step cc) with 3-methyl-but-3-en-1-ol obtained by the recovery process according to the presently claimed invention to obtain combined 3-methyl-but-3-en-1-ol.

In one embodiment, the 3-methyl-but-3-en-1-ol recovered in step C) is combined with the 3-methyl-but-3-en-1-ol obtained from step cc). The combined 3-methyl-but-3-en-1-ol is subjected to a purification method to obtain purified combined 3-methyl-but-3-en-1-ol.

In another embodiment, the purification method is selected from filtration, evaporation, distillation and chromatography, preferably the purification method is distillation.

In yet another embodiment, the distillation for the purification of the combined 3-methyl-but-3-en-1-ol is carried out at a temperature in the range of ≥120° C. to ≤160° C. to obtain purified 3-methyl-but-3-en-1-ol.

In yet another embodiment, the purified 3-methyl-but-3-en-1-ol has a purity of σ98.0 wt. %.

In the following, there is provided a list of embodiments to further illustrate the present disclosure without intending to limit the disclosure to the specific embodiments listed below.

1. A process for recovery of 3-methyl-but-3-en-1-ol from a stream comprising 3-methyl-but-3-en-1-yl formate, ≥0.01 wt. % to ≤10 wt. % water and ≥50 wt. % to ≤70 wt. % methanol each based on the total weight of the stream, comprising at least the steps of:
    A) contacting at least one amine catalyst with the stream to obtain a treated stream;
    B) subjecting the treated stream to a temperature in the range of ≥40° C. to ≤120° C. to obtain 3-methyl-but-3-en-1-ol; and
    C) removing 3-methyl-but-3-en-1-ol from the treated stream.

2. The process according to embodiment 1, wherein the process is a continuous process.

3. The process according to embodiment 1 or 2, wherein the steps A) to C) are carried out simultaneously.

4. The process according to embodiment 1, wherein the stream comprises 3-methyl-but-3-en-1-yl formate in an amount in the range of ≥1 wt. % to ≤25 wt. %, based on the total weight of the stream.

5. The process according to embodiment 1, wherein the methyl formate is continuously removed from the treated stream of step B).

6. The process according to embodiment 1, wherein the stream comprises 3-methyl-but-3-en-1-ol in an amount in the range of ≥0.001 wt. % to ≤10 wt. %, based on the total weight of the stream.

7. The process according to any one of the embodiments 1 to 6, wherein the boiling point of the at least one amine catalyst is in the range of ≥2° C. to ≤130° C.

8. The process according to any one of the embodiments 1 to 7, wherein the at least one amine catalyst is selected from the group consisting of trimethylamine, dimethylamine, triethylamine, diethylamine, triisopropylamine, diisopropylamine, 1-propylamine, butan-2-amine, methylpropan-2-amine, ethane-1,2-diamine, pyridine and piperidine.

9. The process according to embodiment 8, wherein the at least one amine catalyst is trimethylamine or triethylamine.

10. The process according to any one of embodiments 1 to 9, wherein the at least one amine catalyst is present in an amount in the range of ≥0.001 to ≤5.0 wt. %, based on the total weight of the stream.

11. The process according to any one of embodiments 1 to 10, wherein the pH of the treated stream is in the range of pH 7.0 to 9.5.

12. The process for providing the stream of embodiment 1 comprising 3-methyl-but-3-en-1-yl formate, ≥0.01 wt. % to ≤10 wt. % water and ≥50 wt. % to ≤70 wt. % methanol each based on the total weight of the stream, wherein the process comprises at least the steps of:
    a) reacting 2-methylprop-1-ene and formaldehyde to obtain a mixture comprising 3-methyl-but-3-en-1-ol, methanol, water and 3-methyl-but-3-en-1-yl formate;
    b) separating the mixture obtained in step a) into an organic phase comprising at least 3-methyl-but-3-en-1-ol, methanol and 3-methyl-but-3-en-1-yl formate and an aqueous phase comprising water and 10 wt. % 3-methyl-but-3-en-1-ol;
    c) subjecting the organic phase obtained in step b) to a temperature in the range of ≥120° C. to ≤160° C. to separate a light boiling fraction comprising water, methanol, 3-methyl-but-3-en-1-yl formate from 3-methyl-but-3-en-1-ol;
    d) combining the aqueous phase from step b) and the light boiling fraction of step c) and subjecting the combined phases to a temperature in the range of ≥85° C. to ≤105° C. to remove at least 70% water of the total amount of water to obtain a drained stream; and
    e) subjecting the drained stream of step d) to a temperature in the range of ≥85° C. to ≤100° C., to obtain the stream of embodiment 1 comprising 3-methyl-but-3-en-1-yl formate, ≥0.01 wt. % to ≤10 wt. % water and ≥50 wt. % to ≤70 wt. % methanol, each based on the total weight of the stream.

13. The process according to embodiment 12, wherein in step a) the temperature is in the range of ≥150° C. to ≤350° C.

14. The process according to embodiment 13, wherein in step a) the temperature is in the range of ≥200° C. to ≤300° C.

15. The process according to embodiment 12, wherein in step a) the pressure is in the range of 150 bar to 350 bar, preferably in the range of 200 bar to 270 bar.

16. The process according to embodiment 12, wherein in step c) the pressure is in the range of ≥50 to ≤300 mbar.

17. A process for the production of 3-methyl-but-3-en-1-ol comprising at least the step of
   aa) reacting 2-methylprop-1-ene and formaldehyde to obtain a mixture comprising 3-methyl-but-3-en-1-ol, formic acid, methanol and 3-methyl-but-3-en-1-yl formate;
   bb) separating the mixture obtained in step aa) into an organic phase comprising at least 3-methyl-but-3-en-1-ol, methanol and 3-methyl-but-3-en-1-yl formate and an aqueous phase;
   cc) subjecting the organic phase obtained in step bb) to a temperature in the range of ≥120° C. to ≤160° C. to separate a light boiling fraction comprising water, methanol and 3-methyl-but-3-en-1-yl formate from 3-methyl-but-3-en-1-ol; and
   dd) combining 3-methyl-but-3-en-1-ol obtained in step cc) with 3-methyl-but-3-en-1-ol obtained by the process according to any of embodiments 1 to 11 to obtain combined 3-methyl-but-3-en-1-ol.
18. The process according to embodiment 17, further comprising the step ee) of subjecting the combined 3-methyl-but-3-en-1-ol to a purification method to obtain purified combined 3-methyl-but-3-en-1-ol.
19. The process according to embodiment 18, wherein the purification method is distillation.
20. The process according to embodiments 18 or 19, wherein the combined purified 3-methyl-but-3-en-1-ol has a purity 98.0 wt. %.

Having described the invention, a further understanding can be obtained by reference to certain specific examples which are provided herein for the purposes of illustration only. The examples are not intended to be limiting unless otherwise specified.

EXAMPLES

The gas chromatography analysis in each of the Examples was performed under the following conditions.
Apparatus: Agilent 7890B
Column used: DB Wax 30 m, inner diameter 0.32 mm, film thickness 0.25 μm Analysis conditions: 50° C., 5 minutes isotherm—heating rate 6° C./min to 230° C.-230° C., 30 minutes isotherm Example 1

2-Methylprop-1-ene (2053 g), aqueous formaldehyde (200 g; 50 wt. %) and 1.4 g urotropine were placed in an autoclave. The autoclave was sealed, stirred and heated to 270° C. and thus the internal pressure rose to 100 bar. The autoclave was pressurized with nitrogen to 250 bar. The reaction mixture was stirred at 270° C. and 250 bar for 1 h. The reaction mixture was cooled to 25° C. and the pressure was released. The 2-methylprop-1-ene was collected and recycled. The liquid reaction mixture was weighted and analyzed.

Organic upper phase: 370 g

| | |
|---|---|
| 69% = 255 g | 3-methyl-but-3-en-1-ol |
| 0.9% = 3.3 g | formaldehyde |

-continued

| | |
|---|---|
| 20.8% = 77 g | water |
| 2% = 7.4 g | methanol |
| 1.1% = 4.1 g | 3-methyl-but-3-en-1-yl formate |
| 1.2% = 4.4 | 3-methyl-but-2-enal |
| 5% = 5.5 g | side-products |

Aqueous lower phase: 29 g

| | |
|---|---|
| 8% = 2.3 g | 3-methyl-but-3-en-1-ol |
| 4% = 1.16 g | methanol |
| 2% = 0.56 g | side products |
| 86% = 24.9 g | water |

General Method for the Purification of 3-methyl-but-3-en-1-ol

Distillation 1: Use was made of a continuous distillation column and the organic upper phase of the reaction was distilled at a pressure of 1013 mbar with a sump temperature of ≤135° C. and a head temperature of ≥101° C. The reflux ratio for the distillate stream was adjusted to 5:1.

Water, 3-methyl-but-3-en-1-yl formate, methanol and other low boilers were removed with the distillate head stream.

Distillation 2: The sump stream of distillation 1 with 3-methyl-but-3-en-1-ol, 3-methyl-but-2-enal and side products was purified in a distillation column 2 to obtain ≥98.0% of 3-methyl-but-3-en-1-ol and ≤1.5% of 3-methyl-but-2-enal.

Distillation 3: The head stream of water, 3-methyl-but-3-en-1-yl formate, methanol and other low boilers was combined with the aqueous lower phase of the reaction and the two-phase mixture was fed into the distillation column 3.

The distillation column was operated at a pressure 1023 mbar with a sump temperature of 100° C. and a reflux ratio of 25:1. The temperature in the stripping section of the column was maintained at 95° C. to 100° C. The organic components (including methanol, 3-methyl-but-3-en-1-yl formate, 3-methyl-but-3-en-1-ol) were depleted and waste water with a content of <1% of organic compounds were removed at the sump of the column.

The temperature in the rectifying section of the column was maintained at 80° C. to 95° C. and water was depleted to obtain a stream of 3-methyl-but-3-en-1-yl formate, ≥0.01 wt. % to ≤10 wt. % water and ≥50 wt. % to ≤70 wt. % methanol, each based on the total weight of the stream.

A stream of 3-methyl-but-3-en-1-yl formate, ≥0.01 wt. % to ≤10 wt. % water and ≥50 wt. % to ≤70 wt. % methanol, each based on the total weight of the stream, was transesterified in the presence of an amine catalyst as illustrated in the Table 2-5. The reactions were performed in a 250 ml flask, equipped with a stirrer, a gas injection pipe for nitrogen-stripping and a distillation column. The reaction was heated with an external oil bath. The progress of the reaction was monitored by gas chromatography, the pH-value was controlled and monitored with a pH electrode.

The recovered 3-methyl-but-3-en-1-ol was sent to the distillation column 1.

TABLE 2

Process for recovery of 3-methyl-but-3-en-1-ol without the removal of methyl formate
Temperature: 50° C
Amine catalyst: Trimethylamine, 1 wt. %
Starting sample: 6.2 wt. % water, 69.47 wt. % methanol, 12.1 area %
3-methyl-but-3-en-1-yl formate and 3.62 wt. % 3-methyl-but-3-en-1-ol.
Starting reaction mass: 90 g
pH: 9.0

| reaction time (minutes) | water content (wt. %) | reaction mass (g) | methanol (wt. %) | 3-methyl-but-3-en-1-yl formate (area %) | 3-methyl-but-3-en-1-ol (wt. %) |
|---|---|---|---|---|---|
| 10 | 6.2 |  | 69.71 | 10.03 | 4.8 |
| 20 | n.d. |  | 68.59 | 8.61 | 5.51 |
| 30 | n.d. |  | 71.07 | 7.36 | 6.33 |
| 40 | n.d. |  | 70.14 | 6.56 | 6.78 |
| 50 | n.d. |  | 66.74 | 5.69 | 7.12 |
| 60 | 6.2 | 89 | 69.70 | 4.65 | 7.79 |

TABLE 3

Process for recovery of 3-methyl-but-3-en-1-ol with the continuous removal of methyl formate
Temperature: 50° C
Amine catalyst: Trimethylamine, 1 wt. %
Operation: nitrogen stripping (1 l/h)
Starting sample: 6.78 wt. % water, 68.93 wt. % methanol, 6.14 area % methyl formate,
10.43 area % 3-methyl-but-3-en-1-yl formate and 4.60 wt. % 3-methyl-but-3-en-1-ol.
Starting reaction mass: 96 g
pH: 9.5

| reaction time (minutes) | water content (wt. %) | reaction mass (g) | methyl formate (area %) | methanol (wt. %) | 3-methyl-but-3-en-1-yl formate (area %) | 3-methyl-but-3-en-1-ol (wt. %) |
|---|---|---|---|---|---|---|
| 10 | 6.78 |  | 3.54 | 70.64 | 8.03 | 6.92 |
| 20 | n.d. |  | 2.43 | 75.42 | 5.64 | 8.92 |
| 30 | n.d. |  | 1.95 | 73.40 | 4.69 | 9.60 |
| 40 | n.d. |  | 0.39 | 75.65 | 3.04 | 10.90 |
| 50 | n.d. |  | 0.68 | 76.50 | 2.15 | 11.83 |
| 60 | n.d. |  | 0.51 | 77.43 | 1.60 | 12.51 |
| 150 | 0.1 | 65 | 0.0 | 71.56 | 0.0 | 16.04 |

TABLE 4

Process for recovery of 3-methyl-but-3-en-1-ol with the continuous removal of methyl formate
Temperature: 60° C
Amine catalyst: Trimethylamine, 3 wt. %
Starting sample: 5.90 wt. % water, 66.89 wt. % methanol, 6.28 area % methyl formate,
8.47 area % 3-methyl-but-3-en-1-yl formate and 5.49 wt. % 3-methyl-but-3-en-1-ol.
Starting reaction mass: 73 g
pH: 8.7-9

| reaction time (minutes) | water content (wt. %) | reaction mass (g) | methyl formate (area %) | methanol (wt. %) | 3-methyl-but-3-en-1-yl formate (area %) | 3-methyl-but-3-en-1-ol (wt. %) |
|---|---|---|---|---|---|---|
| 15 | n.d. |  | 6.28 | 66.27 | 4.76 | 7.56 |
| 30 | n.d. |  | 5.99 | 78.69 | 3.71 | 9.71 |
| 45 | n.d. |  | 5.92 | 67.06 | 3.03 | 8.60 |
| 60 | n.d. |  | 5.74 | 66.54 | 2.21 | 9.10 |
| 120 | 5.80 | 59 | 5.6 | 67.08 | 0.84 | 9.96 |

Examples Outside the Scope of the Presently Claimed Invention

TABLE 5

Process for recovery of 3-methyl-but-3-en-1-ol with the continuous removal of methyl formate in the absence of amine catalyst
Temperature: 60° C
Starting sample: 4.80 wt. % water, 56.72 wt. % methanol, 4.31 area % methyl formate, 14.33 area % 3-methyl-but-3-en-1-yl formate and 5.49 wt. % 3-methyl-but-3-en-1-ol.
Starting reaction mass: 209.0 g
pH: 9.1

| reaction time (minutes) | water content (wt. %) | reaction mass (g) | methyl formate (area %) | methanol (wt. %) | 3-methyl-but-3-en-1-yl formate (area %) | 3-methyl-but-3-en-1-ol (wt. %) |
| --- | --- | --- | --- | --- | --- | --- |
| 15 | n.d. |  | 3.26 | 57.23 | 10.44 | 8.68 |
| 30 | n.d. |  | 2.49 | 58.15 | 10.05 | 9.91 |
| 45 | n.d. |  | 1.94 | 58.40 | 9.35 | 11.31 |
| 60 | n.d. |  | 1.67 | 58.55 | 8.93 | 12.22 |
| 150 | 5.90 | 156.5 | 1.17 | 58.50 | 6.68 | 15.22 |
| Overnight | 5.90 |  | 1.59 | 58.19 | 4.14 | 17.58 |

TABLE 6

Process for recovery of 3-methyl-but-3-en-1-ol in the absence of amine catalyst
Temperature: 20° C
Starting sample: 4.20 wt. % water, 57.00 area % methanol, 16.70 area % 3-methyl-but-3-en-1-yl formate and 0.97 wt. % 3-methyl-but-3-en-1-ol.
Starting reaction mass: 100 g
pH: 8.5

| reaction time (h) | water content (wt. %) | methanol (area %) | 3-methyl-but-3-en-1-yl formate (area %) | 3-methyl-but-3-en-1-ol (wt. %) |
| --- | --- | --- | --- | --- |
| 3.0 | n.d. | 57.0 | 16.40 | 1.97 |
| 5.50 | n.d. | 59.0 | 15.10 | 2.71 |
| 26.50 | 4.2 | 57.0 | 11.20 | 6.5 |

TABLE 7

Process for recovery of 3-methyl-but-3-en-1-ol in the presence of acid -
No transesterification, i.e. no formation of 3-methyl-but-3-en-1-ol, was observed in acidic media.
Temperature: 20° C
Acid: Formic acid
Starting sample: 5.01 wt. % water, 69.90 wt. % methanol, 6.40 area % 3-methyl-but-3-en-1-yl formate and 10.65 wt. % 3-methyl-but-3-en-1-ol.
Starting reaction mass: 100 g
Starting pH: 8.14, the pH value of several samples was adjusted by addition of formic acid.
The samples were stirred for 72 h.

|  | pH-Value | methanol (wt.-%) | 3-methyl-but-3-en-1-yl formate (area %) | 3-methyl-but-3-en-1-ol (wt. %) |
| --- | --- | --- | --- | --- |
| Sample 1 addition formic acid: 0.09 g | 6.82 | 71.9 | 6.6 | 5.57 |
| Sample 2 addition formic acid: 0.18 g | 5.9 | 71.1 | 6.63 | 5.53 |
| Sample 3 addition formic acid: 0.65 g | 5.0 | 70.6 | 6.64 | 5.5 |
| Sample 4 addition formic acid: 1.64 g | 4.5 | 69.5 | 6.64 | 5.44 |
| Sample 5 addition formic acid: 2.91 g | 4.1 | 70.6 | 6.61 | 5.65 |

The invention claimed is:

1. A process for recovery of 3-methyl-but-3-en-1-ol from a stream comprising 3-methyl-but-3-en-1-yl formate, ≥0.01 wt. % to ≤10 wt. % water and ≥50 wt. % to <70 wt. % methanol, each based on the total weight of the stream, comprising at least the steps of: contacting at least one amine catalyst with the stream to obtain a treated stream;
   A) subjecting the treated stream to a temperature in the range of ≥40° C. to ≤120° C. to obtain 3-methyl-but-3-en-1-ol; and
   B) removing 3-methyl-but-3-en-1-ol from the treated stream.

2. The process according to claim 1, wherein the process is a continuous process.

3. The process according to claim 1, wherein the steps A) and B) are carried out simultaneously.

4. The process according to claim 1, wherein the stream comprises 3-methyl-but-3-en-1-yl formate in an amount in the ≥1 wt. % to ≤25 wt. %, based on the total weight of the stream.

5. The process according to claim 1, wherein the methyl formate 1s continuously removed from the treated stream of step B).

6. The process according to claim 1, wherein the stream comprises 3-methyl-but-3-en-1-ol in an amount in the range of ≥0.001 wt. % to ≤10 wt. %, based on the total weight of the stream.

7. The process according to claim 1, wherein the boiling point of the at least one amine catalyst is in the range of ≥2° C. to ≤130° C.

8. The process according to claim 1, wherein the at least one amine catalyst is selected from the group consisting of trimethylamine, dimethylamine, triethylamine, diethylamine, triisopropylamine, diisopropylamine, 1-propylamine, butan-2-amine, methylpropan-2-amine, ethane-1,2-diamine, pyridine and piperidine.

9. The process according to claim 8, wherein the at least one amine catalyst is trimethylamine or triethylamine.

10. The process according to claim 1, wherein the at least one amine catalyst is present in an amount in the range of ≥0.001 to ≤5.0 wt. %, based on the total weight of the stream.

11. The process according to claim 1, wherein the pH of the treated stream is in the range of pH 7.0 to 9.5.

12. The process according to claim 1, wherein the stream is obtained by a method comprising at least the steps of:
   a) reacting 2-methylprop-1-ene and formaldehyde to obtain a mixture comprising 3-methyl-but-3-en-1-ol, methanol, water and 3-methyl-but-3-en-1-yl formate;
   b) separating the mixture obtained in step a) into an organic phase comprising at least 3-methyl-but-3-en-1-ol, methanol and 3-methyl-but-3-en-1-yl formate and an aqueous phase comprising water and ≤10 wt. % 3-methyl-but-3-en-1-ol;
   c) subjecting the organic phase obtained in step b) to a temperature in the range of ≥120° C. to ≤160° C. to separate a light boiling fraction comprising water, methanol, 3-methyl-but-3-en-1-yl formate from 3-methyl-but-3-en-1-ol;
   d) combining the aqueous phase from step b) and the light boiling fraction of step c) and subjecting the combined phases to a temperature in the range of ≥85° C. to ≤105° C. to remove at least 70% water of the total amount of water to obtain a drained stream; and
   e) subjecting the drained stream of step d) to a temperature in the range of ≥85° C. to ≤100° C., to obtain the stream of claim 1 comprising 3-methyl-but-3-en-1-yl formate, ≥0.01 wt. % to ≤10 wt. % water and ≥50 wt. % to ≤70 wt. % methanol, each based on the total weight of the stream.

13. A process for the production of 3-methyl-but-3-en-1-ol comprising at least the step of
   aa) reacting 2-methylprop-1-ene and formaldehyde to obtain a mixture comprising 3-methyl-but-3-en-1-ol, formic acid, methanol and 3-methyl-but-3-en-1-yl formate;
   bb) separating the mixture obtained in step aa) into an organic phase comprising at least 3-methyl-but-3-en-1-ol, methanol and 3-methyl-but-3-en-1-yl formate and an aqueous phase;
   cc) subjecting the organic phase obtained in step bb) to a temperature in the range of ≥120° C. to ≤160° C. to separate a light boiling fraction comprising water, methanol and 3-methyl-but-3-en-1-yl formate from 3-methyl-but-3-en-1-ol; and
   dd) combining 3-methyl-but-3-en-1-ol obtained in step cc) with 3-methyl-but-3-en-1-ol obtained by the process according to claim 1 to obtain combined 3-methyl-but-3-en-1-ol .

14. The process according to claim 13, further comprising the step ee) of subjecting the combined 3-methyl-but-3-en-1-ol to a purification method to obtain purified combined 3-methyl-but-3-en-1-ol.

15. The process according to claim 14, wherein the purification method is distillation.

16. The process according to claim 14, wherein the purified combined 3-methyl-but-3-en-1-ol has a purity ≥98.0 wt. %.

* * * * *